United States Patent [19]
Houghton

[11] Patent Number: 5,836,914
[45] Date of Patent: Nov. 17, 1998

[54] METHOD AND APPARATUS FOR VARIABLY REGULATING THE LENGTH OF A COMBINED SPINAL-EPIDURAL NEEDLE

[75] Inventor: Frederick C. Houghton, Sussex, N.J.

[73] Assignee: Becton Dickinson and Company, Franklin Lakes, N.J.

[21] Appl. No.: 529,301

[22] Filed: Sep. 15, 1995

[51] Int. Cl.$^6$ .................................................. A61M 5/00
[52] U.S. Cl. ........................................... 604/117; 604/158
[58] Field of Search .............................. 604/51, 117, 164, 604/165, 158, 159, 160, 161, 171, 272

[56] References Cited

U.S. PATENT DOCUMENTS

| | | | |
|---|---|---|---|
| 1,213,001 | 1/1917 | Philips | 604/117 X |
| 2,047,010 | 7/1936 | Dickinson | 604/117 X |
| 3,356,089 | 12/1967 | Francis | 128/221 |
| 3,406,687 | 10/1968 | Moyer | 128/221 |
| 3,964,480 | 6/1976 | Froning | 128/215 |
| 4,645,491 | 2/1987 | Evans | 604/158 |
| 4,760,847 | 8/1988 | Vaillancourt | 128/329 |
| 4,801,293 | 1/1989 | Jackson | 604/51 |
| 4,860,742 | 8/1989 | Park et al. | 604/159 X |
| 4,919,653 | 4/1990 | Martinez et al. | 604/117 |
| 4,940,458 | 7/1990 | Cohn | 604/51 |
| 4,994,042 | 2/1991 | Vadher | 604/165 |
| 5,085,631 | 2/1992 | Leighton | 604/28 |
| 5,106,376 | 4/1992 | Mononen et al. | 604/164 |
| 5,135,525 | 8/1992 | Biscoping et al. | 604/51 |
| 5,141,496 | 8/1992 | Dalto et al. | 604/117 |
| 5,195,526 | 3/1993 | Michelson | 128/654 |
| 5,257,972 | 11/1993 | Gurmarnik | 604/51 |
| 5,290,243 | 3/1994 | Chodorow et al. | 604/165 |
| 5,312,375 | 5/1994 | Gurmarnik | 604/264 |
| 5,374,252 | 12/1994 | Banks et al. | 604/158 |
| 5,611,778 | 3/1997 | Brinon | 604/158 X |

OTHER PUBLICATIONS

Use of 29–Gauge Spinal Needles and a Fixation Device with Combined Spinal Epidural Technique, J. Simsa, Acta Anaesthesiologica Scandinavica 38 (1994) pp. 439–441.

*Primary Examiner*—Wynn Wood Coggins
*Assistant Examiner*—Jennifer R. Sadula
*Attorney, Agent, or Firm*—Arthur D. Dawson

[57] ABSTRACT

A regulating device for variably regulating the length of a combined spinal epidural needle and the method of practicing same is disclosed. In one variant, the regulating device features a pair of substantially concentricity disposed sliding members to which each of the epidural needle and spinal needle may be separately fitted. A spring element is provided to selectably engage the spinal needle. The spring element includes one end fixed to the sliding member securing the epidural needle, a free end manipulable by a user, and at least one passage or opening disposed between the fixed and free ends through which the spinal needle passes. The opening is configured to permit either gripping or free sliding of the spinal needle depending on the practitioner's actuation of the spring element. By actuation of the spring element, the practitioner may control axial movement between the sliding members, thereby regulating the extension of the spinal needle relative to the epidural needle. The sliding members may be configured in a variety of shapes or dimensions to accommodate various combinations of spinal and epidural needles. The device may be provided pre-assembled with either one or both of the spinal needle or epidural needle, or it may be employed with a spinal needle, epidural needle, or both separately sourced.

22 Claims, 13 Drawing Sheets

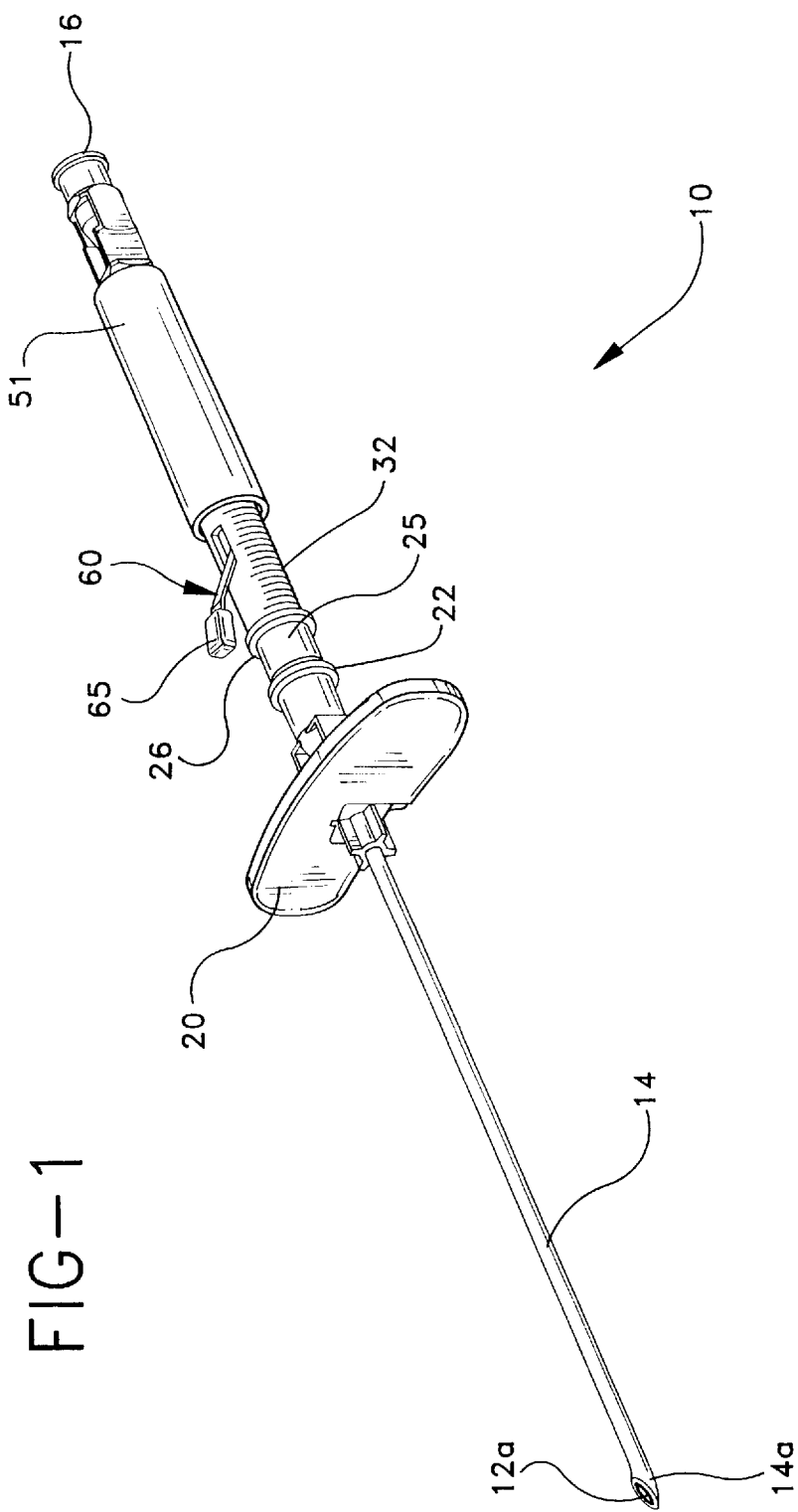

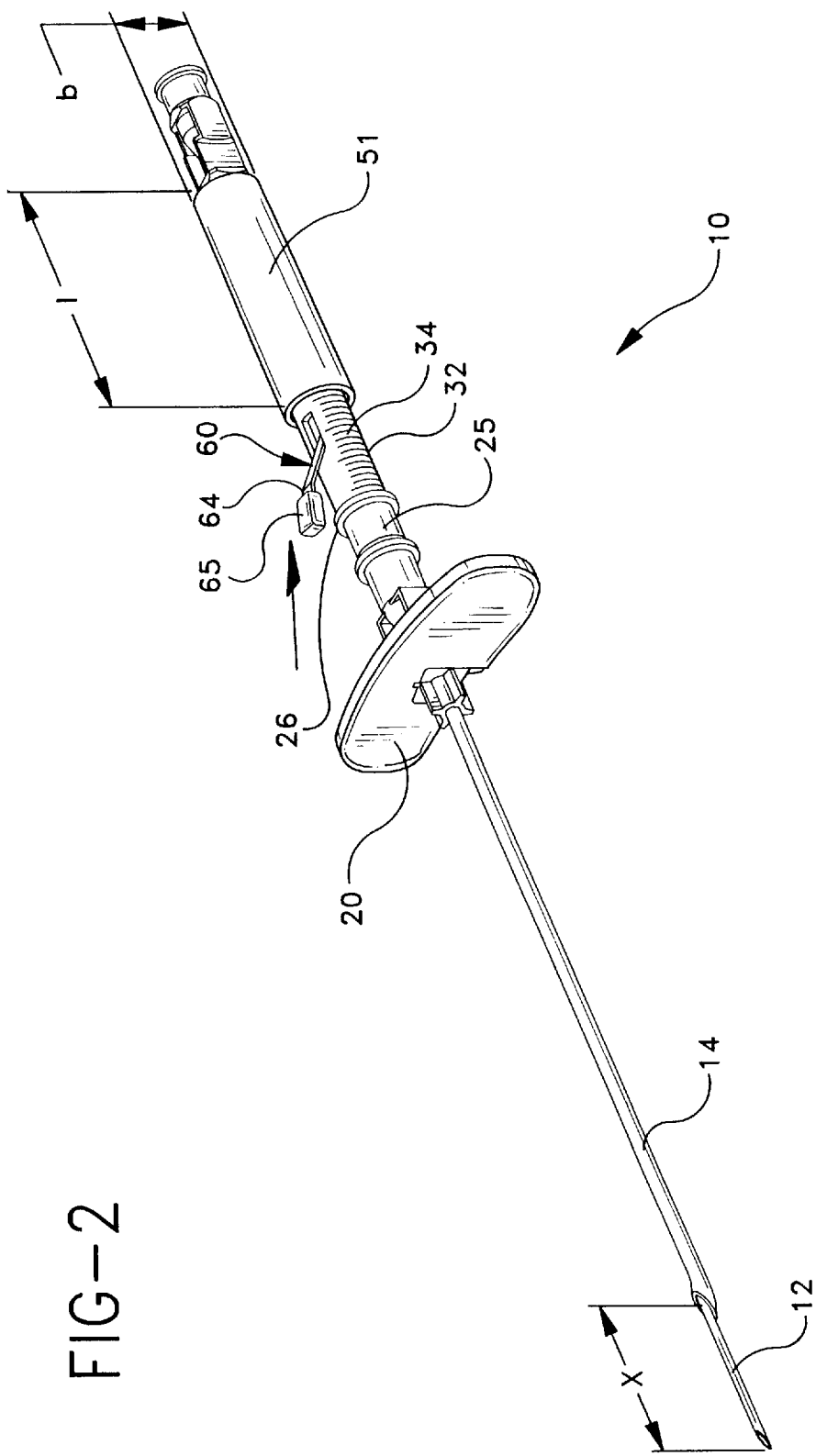

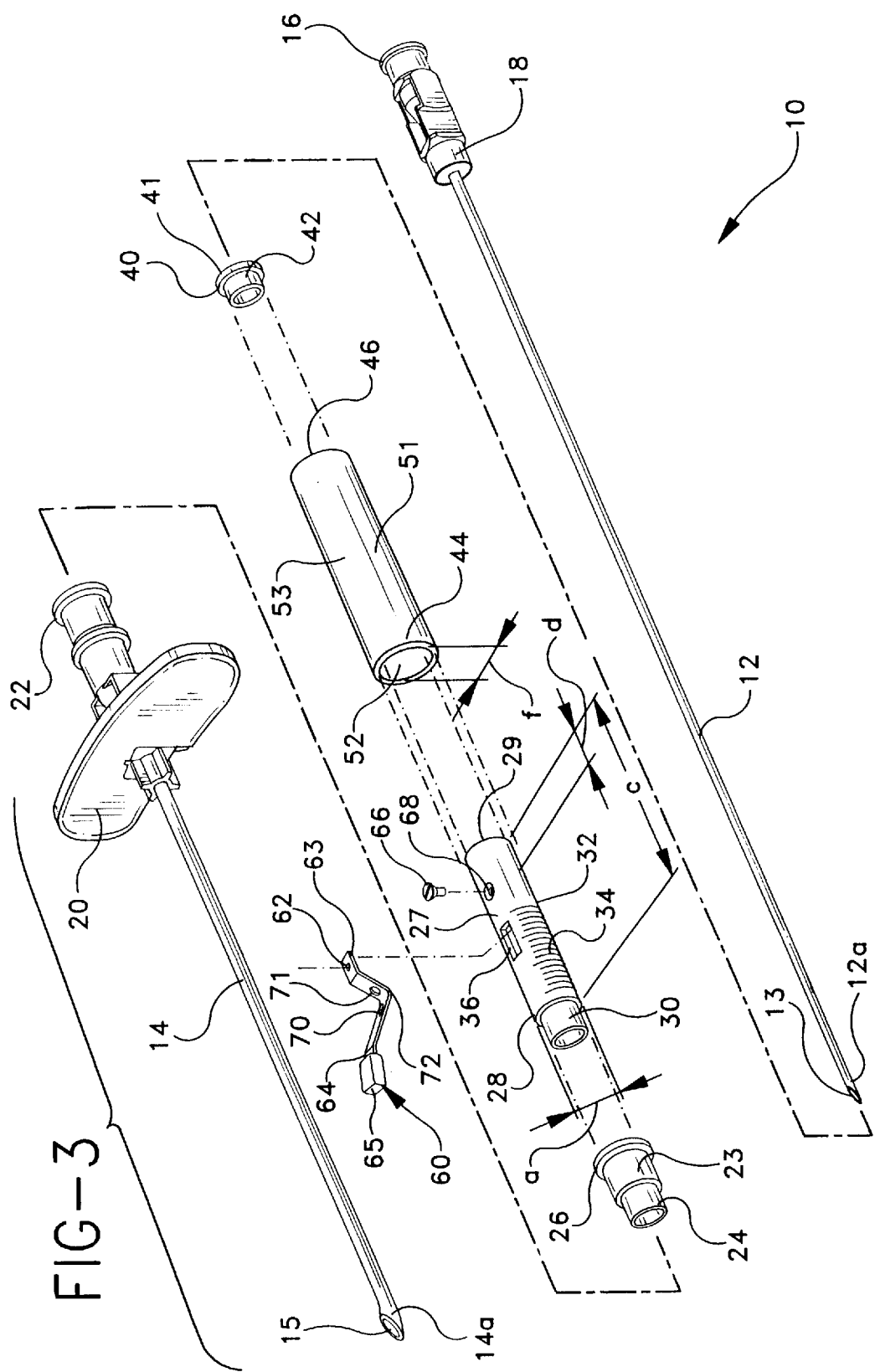

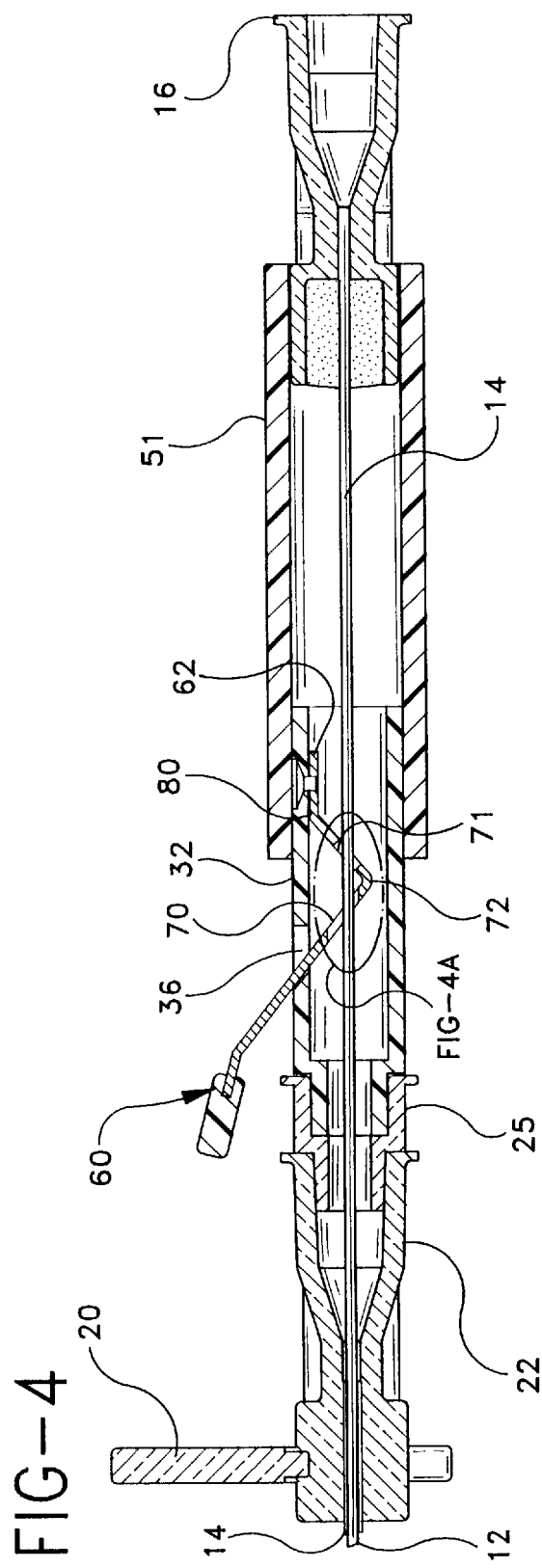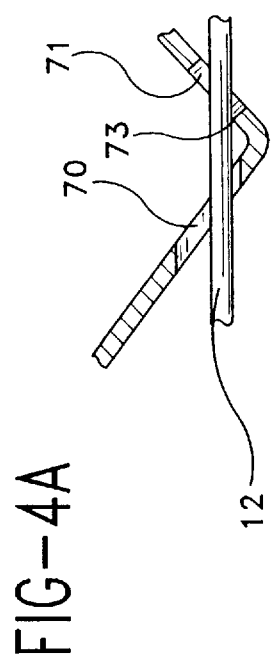

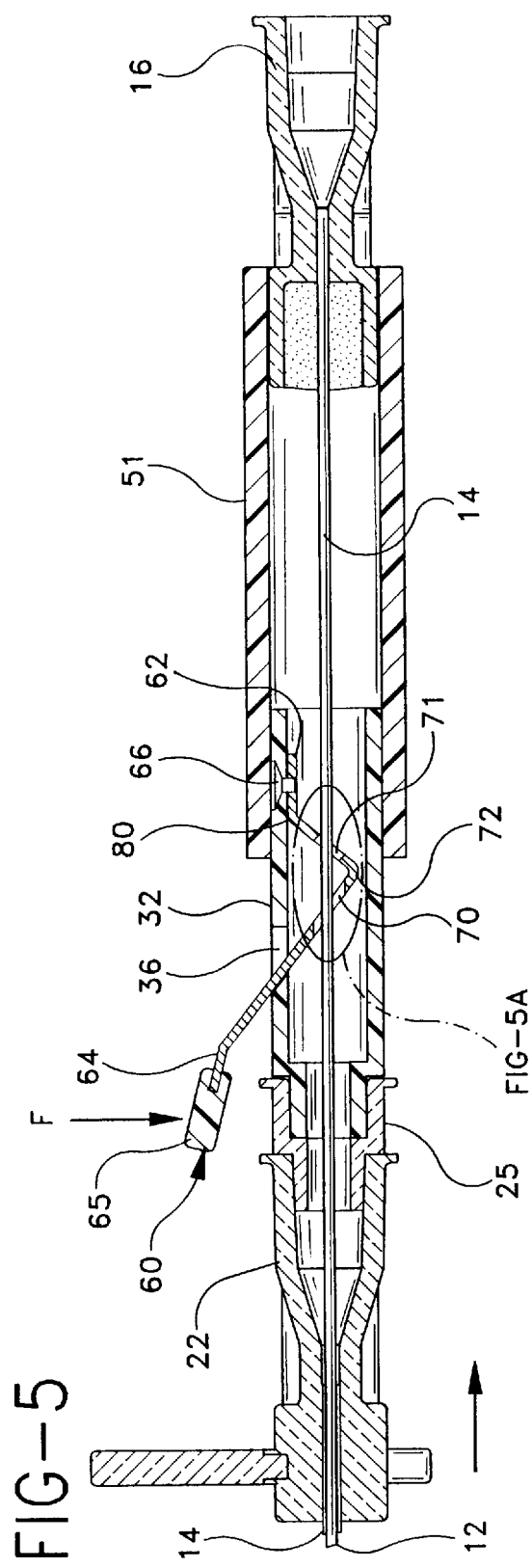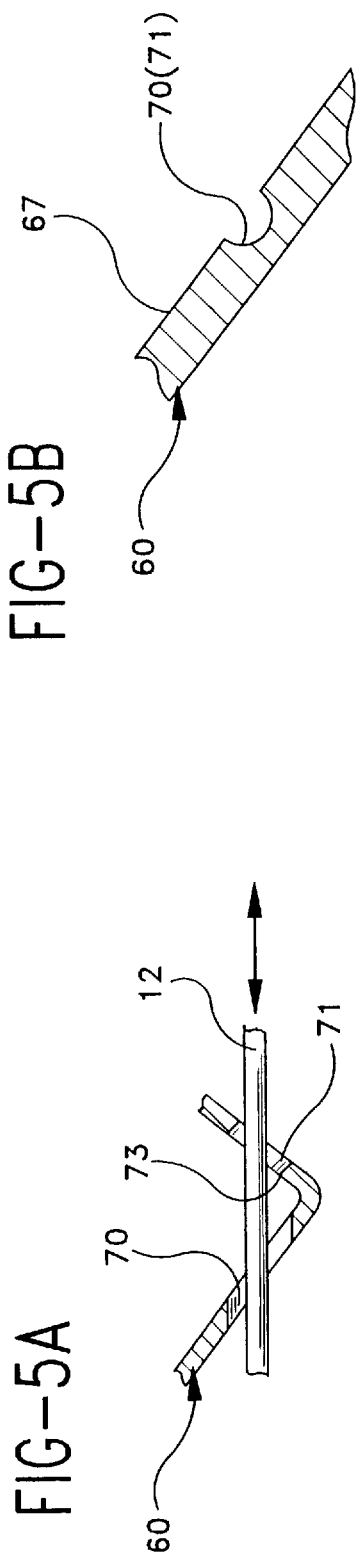

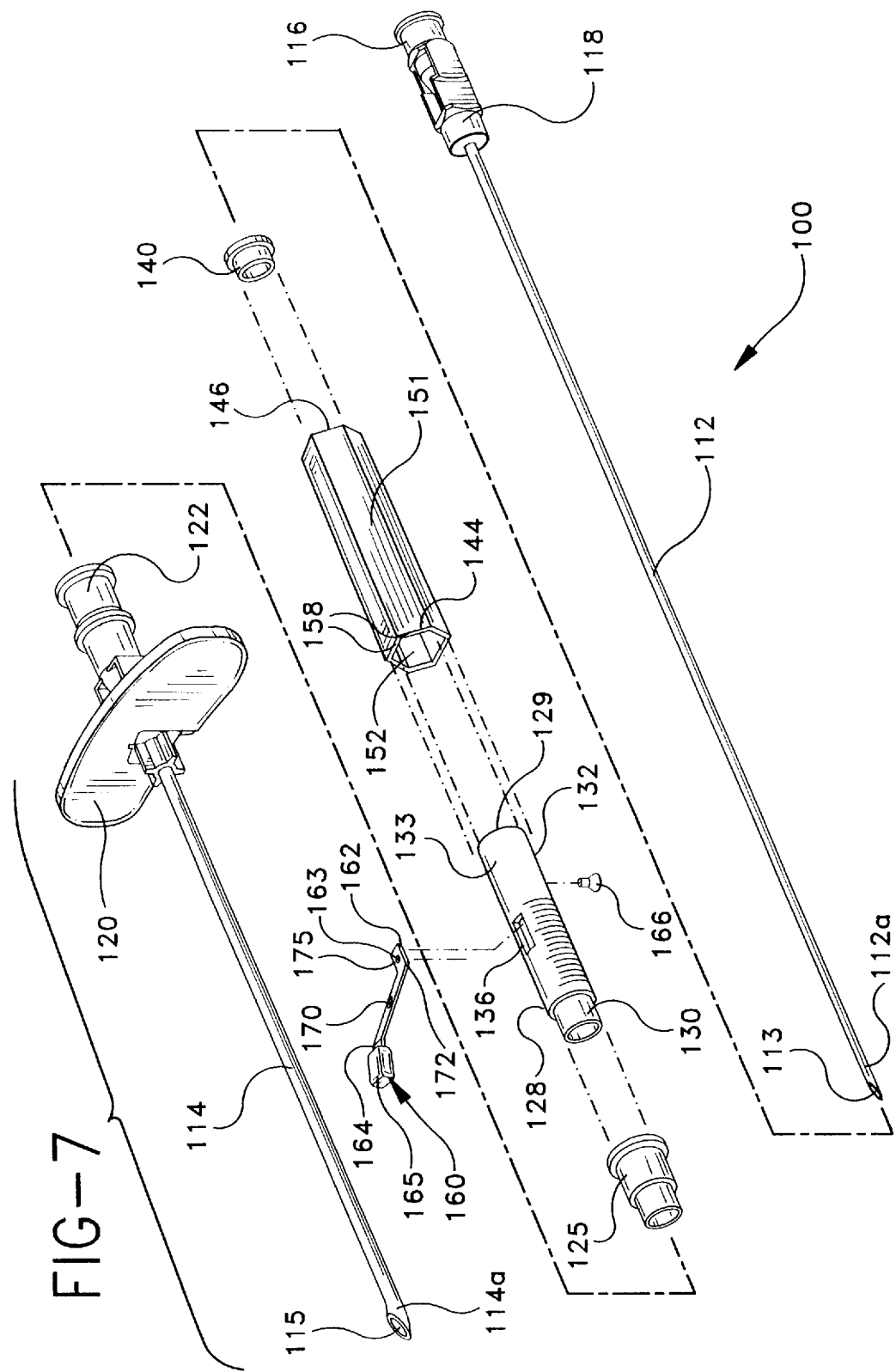

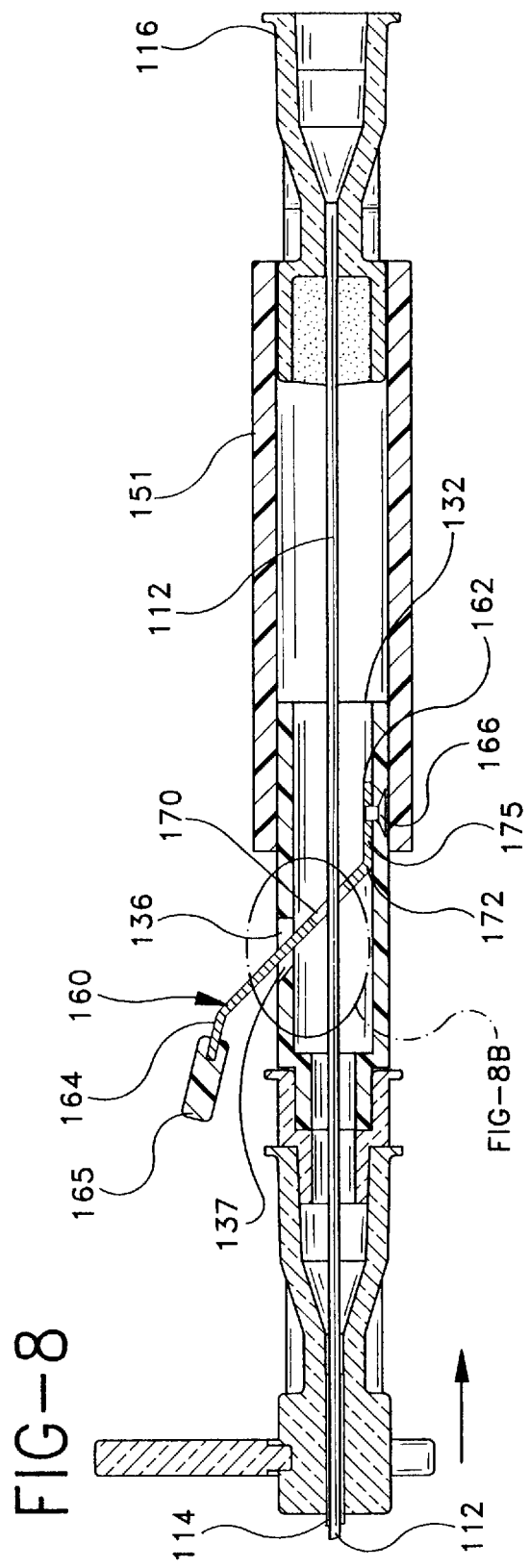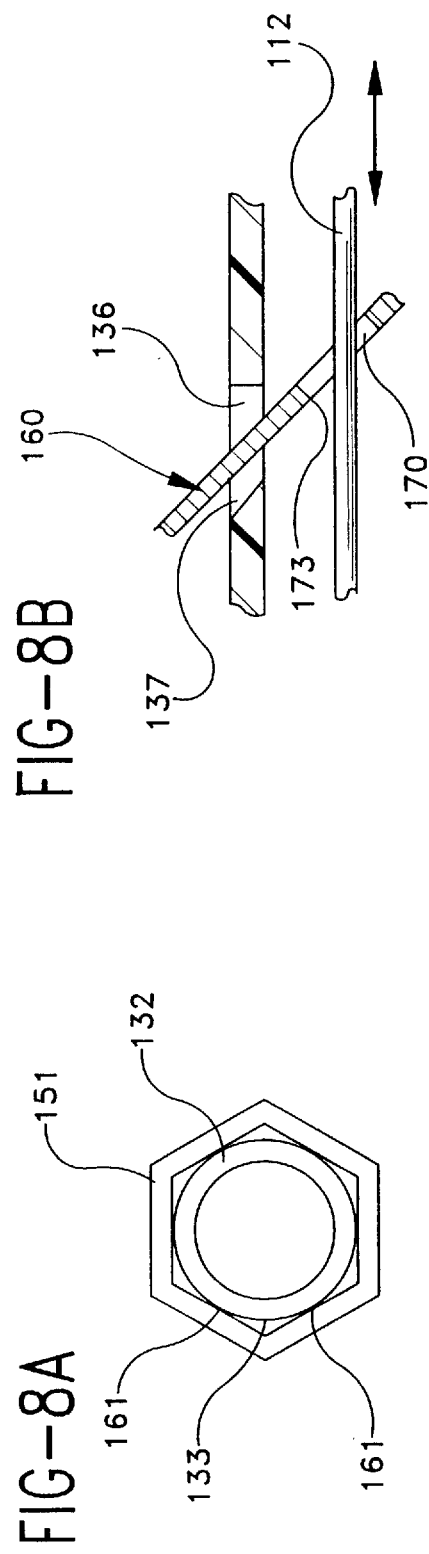

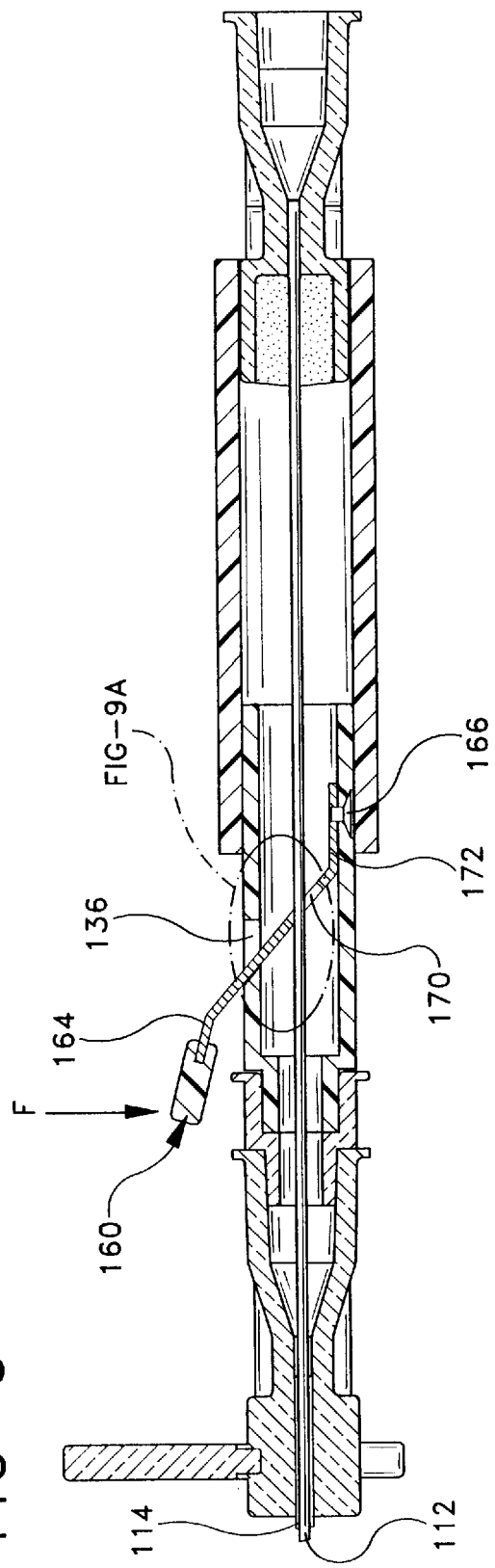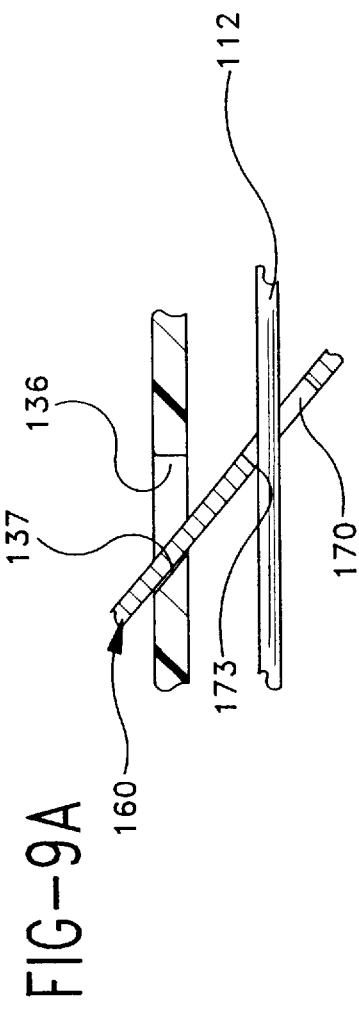

METHOD AND APPARATUS FOR VARIABLY REGULATING THE LENGTH OF A COMBINED SPINAL-EPIDURAL NEEDLE

FIELD OF THE INVENTION

This invention relates to a combined spinal-epidural needle for delivery of a medicament to the subarachnoid space, and more particularly, to a method and apparatus for adjusting the extension of a spinal needle relative to the epidural needle during a procedure for delivering medicament to the subarachnoid space.

BACKGROUND

As is known in the art, there exist two basic techniques for introducing injectable medicament into the spinal area of a patient. Both of these techniques have their own unique advantages and disadvantages and both can be used to create spinal anesthesia or analgesia. In both of these procedures, of course, the medicaments can be any type of liquid therapeutic material including antibiotics, steroids or the like. In general, however, the medicaments are agents used for anesthesia and/or analgesia.

The first procedure, known as the "epidural" technique, employs an epidural needle to deliver medicament to the epidural space of the patient. Certain epidural needles feature a curved distal end. Certain drawbacks exist with this technique. Because the medicament must percolate through semi-liquid fat to reach the nerve roots, the onset of the anesthetic block is oftentimes slow. Moreover, the potential exists for toxicity caused by the relatively large doses of medicament necessary to obtain an adequate block. After the initial dosage, a catheter is oftentimes inserted through the epidural needle into the epidural space to provide sustained or prolonged anesthesialanalgesia to the patient.

The second procedure, known in the art as the "spinal" or "subarachnoid" technique, typically employs a relatively small gauge needle to deliver medicaments directly to the subarachnoid space of the spinal column. Because the anesthetic is delivered directly to the nerve roots, the onset of anesthetic effect is quite rapid, and the block achieved by the spinal technique is often deeper than that possible employing the epidural technique.

The major disadvantage of the spinal technique relates to postoperative side effects. Unlike the epidural procedure, in the spinal technique, the dura mater must be punctured to reach the subarachnoid space. The resultant leakage of cerebrospinal fluid ("CSF") through the puncture oftentimes leads to severe postoperative headaches, known as "postdural puncture headache" ("PDPH"). In addition, while hypotension can result from either of the epidural or spinal techniques, it is believed that the rapid onset of the block in the spinal procedure causes a higher degree of hypotension than the epidural technique. Moreover, unlike the epidural procedure, which typically employs a catheter for continuous epidural blockage, a single shot spinal needle is often unable to extend the anesthetic block, once fixed.

A survey of previous patent literature reports in this general area may be found, for instance, in U.S. Pat. No. 5,085,631, which is directed to a method for placement of a subarachnoid catheter that utilizes a three component apparatus having an outer needle, an inner needle, and a catheter intermediate the two needles.

In order to alleviate the disadvantages associated with both procedures while providing the advantages of each, a combined spinal-epidural technique, or "CSE", has been developed. In CSE, an epidural needle is inserted into the patient in the usual manner and advanced to the epidural space without puncturing the dura mater. Next, steadying his or her hand against the patient's back and using the fixed epidural needle as an introducer, a smaller gauge spinal needle is inserted through the lumen of the epidural needle and advanced so that the distal end of the spinal needle crosses the epidural space. The practitioner, relying on his sense of touch, continues to insert the spinal needle until the distal end is felt to puncture the dura mater and enter into the subarachnoid space. A "pop" sensation is often felt at the hub of the spinal needle by the practitioner when the dura mater has been punctured. As confirmation of proper placement in the subarachnoid space, the practitioner will normally look for the appearance of CSF at the proximal end of the spinal needle by removing the stylet of the spinal needle.

Spinal anesthetic is administered in the usual manner, and the spinal needle is then withdrawn without displacing the epidural needle. Next, an epidural catheter is introduced through the epidural needle into the epidural space, and the epidural needle is thereafter removed from the back of the patient. Lastly, the epidural catheter is secured in place by taping same to the back of the patient.

In general, the CSE technique provides the practitioner with the benefits associated with the individualized epidural or spinal techniques while offsetting the disadvantages experienced by each. The surgeon is able to gain the advantages of rapid onset of a deep block provided by the spinal procedure. The epidural catheter serves to provide sustained anesthetic effect and extend the block provided by the spinal anesthetic. The catheter also enhances the practitioner's options and choices in administering operative anesthetic or postoperative pain relief. For example, the practitioner is able to administer a spinal anesthetic alone or in combination with epidural anesthetics and/or analgesics. Moreover, the practitioner can choose from a variety of medicaments or combinations thereof, with various rates of delivery, not being limited by the single injection of the spinal technique alone.

While providing the practitioner with a ready way to administer quality anesthetic relief to the patient, a number of drawbacks exist with current CSE practice. The CSE procedure is typically dependent on the individualized practitioner's experience with the method which, in turn, depends on the number and types of patients the doctor has had experience with. The exigencies of the operating environmental also greatly affect the procedure. As previously explained, CSE is performed by the relative insertion of two needles of differing gauges. Because the spinal needle is free to slide within the epidural needle, which itself is only retained by the dura mater once inserted, the danger exists that the spinal needle will be displaced during administration of the anesthetic. Thus, the doctor is required to utilize both hands, one to steady the spinal needle against the patient's body, the other hand to steady the syringe attached to the proximal end of the spinal needle. He must also utilize both hands when locking the spinal needle into place with the epidural needle. Because the doctor must steady his or her hand against the patient's back during insertion, smooth relative sliding is oftentimes difficult to achieve. Adequate tactile feedback, necessary to permit the practitioner to assess relative needle insertion, is also heavily dependent on the exigencies of the operating environment, which can vary at a moment's notice.

In addition, it will be observed that human body structures differ. The relative dimensions of the body, and particularly those defining the epidural space, the thickness of the dura mater, and the distance to the subarachnoid space, will vary. The doctor's appreciation of these dimensions is critical to proper placement of the needles in the appropriate locations, and in particular, to avoid inadvertent puncture of the dura mater.

Moreover, the practitioner not only has to rely on his relative experience to make sure that the spinal needle is extended sufficiently through the dura mater, he must do so with two separate needles that may not often provide him with either sufficient tactile feedback or a discernible way to gauge relative insertion. A typical pencil-point spinal needle such as a Whitacre needle cannot always aspirate CSF, even when the dura mater is felt to "pop." In this situation, to be absolutely sure that the needles are properly placed, the practitioner must often withdraw both needles, repositioning them to re-identify the epidural space and, hence, the subarachnoid. This can cause unnecessary discomfort to both patient and practitioner.

Furthermore, in some situations practitioners will not need the full degree of spinal needle extension provided when the hubs of the spinal and epidural needles engage. When this type of situation occurs, the practitioner is forced to overcome a potentially unsafe and unsecure condition caused by a portion of the spinal needle protruding unsupported from the hub of the epidural needle.

The aforementioned difficulties can be amplified in that CSE is sometimes performed with individualized epidural and spinal needles sourced from different manufacturers. In these cases, owing to differing dimensions, tolerances, quality of finish or the like, precise sliding action between the needles may be compromised. Moreover, the hubs of differing spinal and epidural needles do not often fit, so that the practitioner cannot be sure of the relative extension achieved by the spinal needle. This can also affect the ability of the practitioner to rotate the spinal needle within the epidural needle in the locked state, useful if the practitioner suspects that the ports of the spinal needle are being blocked by the flap created in the dura mater during entry, or where the practitioner desires to better direct the extent of the anesthetic block provided by the spinal needle. The practitioner might wish to rotate the spinal needle so that the distal point is directed around the four quadrants of the subarachnoid space in an attempt to detect CSF. Faulty hub fit in the locked condition hampers the practitioner's ability to exploit the benefits of rotation.

Some manufacturers have begun to market matched sets of spinal/epidural needles to provide good hub fit and establish a predetermined amount of extension between the spinal and epidural needles when both hubs engage. While to a certain extent alleviating some of the problems encountered with "mixing" needles, the practitioner is still constrained by a fixed extension when the hubs interlock. For some patients, the fixed extension may still be inadequate to reach the dura mater, while for others it may be more than necessary.

Certain attempts in the art have sought to regulate the insertion or placement of a needle into the body. For instance, U.S. Pat. No. 4,940,458 is directed to a placement system for an epidural needle. An internally threaded barrel is provided to guide the externally threaded epidural needle via a knurled wheel at the proximal end of the epidural needle. A pressure monitor serves to advise the practitioner when the epidural needle has entered the epidural space. U.S. Pat. No. 5,312,375 is directed to a set for spinal anesthesia employing an introducer needle and a spinal needle. Either a screw or a toothed clamp arrangement may be provided to secure the spinal needle relative to the introducer needle once the spinal needle has been inserted through the dura mater. An analogous technique employing a metallic wing fixed to the epidural needle, with a relatively large L-shaped metallic bar engaged to the wing with two screws to fixedly adjust the position of the spinal needle relative to the epidural needle, has recently been proposed. See J. Simsa, "Use of 29 gauge spinal needles and a Fixation Device with Combined Spinal Epidural Technique", *ACTA Anaesthesiologica Scandinavia*, 1994 Vol. 38, pp. 439–441. The relative extension of the larger leg of the L-shaped bar past the wing is indicative of the spinal needle extension. Once the spinal needle has been extended to its desired position, a screw on the wing is tightened. None of the aforementioned attempts sufficiently addresses the aforementioned problems of relative spinal needle insertion and inadequate (or non-existent) tactile feedback currently experienced with the CSE procedure.

Now allowed U.S. patent application Ser. No. 08/287,995 filed Aug. 9, 1994 for a "Method and Apparatus for Adjusting the Length of a Combined Spinal Epidural Needle" features a pair of sliding members to which each of the spinal needle and epidural needle are separately affixed. An actuation tab forming a selectably fixed connection between the sliding members is provided. By actuating the tab to unlock the sliding members, the practitioner is able to slide the members respective of one another to vary the length of the spinal needle relative to the epidural needle. While effective in addressing the concerns previously noted, the device of U.S. patent application Ser. No. 08/287,995 necessitates that the practitioner depress the actuation tab with the same hand that manipulates the spinal needle. While to a certain degree subjective, some practitioners may prefer manipulating the actuation tab with the hand not manipulating the spinal needle, in the belief that tactile feedback from the spinal needle is enhanced. Also, the actuating tab mates with one of a plurality of groove elements to lock the spinal needle in a discrete position relative to the epidural needle. While for the most part highly effective in providing the desired spinal needle extension, a practitioner's flexibility would be enhanced if the extension of the spinal needle were continuously variable relative to the epidural needle.

SUMMARY OF THE INVENTION

The present invention alleviates in great part the drawbacks associated with present CSE practice and provides the practitioner with a ready way to precisely monitor the insertion or removal of a spinal needle during CSE, all the while preserving good tactile feedback and fit between the spinal needle and epidural needle.

The invention is directed to a regulating device for extending and/or retracting the spinal needle relative to the epidural needle during CSE. The device, which may be provided as part of a CSE set, or with or attached to one of the spinal needle or epidural needles, or which can be provided as a separate unit for utilization with a separately sourced spinal needle or epidural needle or with a separately sourced CSE set, includes a pair of sliding members to which each of the epidural and spinal needles are separately fixed. The sliding members are disposed to permit relative sliding action between the spinal needle and the epidural needle. In one form, the sliding members may be configured as a pair of concentric tubes slidably disposed relative to one another, with the epidural needle secured to the innermost tube and the spinal needle secured to the outermost tube.

A spring element may be provided for regulating the extension between the spinal needle and the epidural needle.

To allow a practitioner maximal tactile feedback during manipulation of the spinal needle, the spring element is configured for actuation by the hand which is not manipulating the sliding member to which the spinal needle is attached. In one configuration, the spring element may be formed from a piece of flattened spring steel and features one end fixed to the innermost tube, and a free end disposed for user manipulation through a slot provided in the innermost tube. The spring element also includes at least one passage or opening intermediate the fixed and free ends through which the spinal needle passes. Depending on the practitioner's manipulation of the spring element, the opening is displaced relative to the spinal needle to: (a) permit the spinal needle to freely travel through the opening, allowing the practitioner to slide the outermost tube relative to the innermost tube to vary the extension of the spinal needle relative to the epidural needle; or (b) grip the spinal needle so as to lock its position relative to the epidural needle. Because there are no discrete locking locations, the locking action of the spring element upon the spinal needle is continuously variable along the entire length of the spinal needle, providing an unlimited number of positions of the spinal needle relative to the epidural needle.

The spring element may be configured such that the spinal needle is first locked in place, being gripped by the opening until a practitioner actuates the free end to release the opening from engagement with the spinal needle. Alternately, the spring element can be configured such that the spinal needle freely passes through the passage or opening until such time as the practitioner acts upon the spring element to lock the opening against the spinal needle. Overall, it will be observed that the practitioner may manipulate the spinal needle with one hand while activating the spring element with the other, thereby avoiding any reduction in tactile feedback caused by same-handed manipulation of the structure locking the spinal needle in place.

Markings formed on the outside surface of the innermost tube provide the practitioner with visual indication of both the alignment of the distal tips of the spinal and epidural needles and with the relative extension length of the spinal needle relative to the epidural needle.

If desired, the interior surface of the outermost tube or, conversely, the exterior surface of the innermost tube, may be structured with a plurality of planar surface portions, with the opposing surface being relatively cylindrical. The mating of a planar surface portion with a rounded surface portion provides point contact between the inner and outer tubes, reducing the engagement surface area between the tubes, and, hence, the frictional resistance between the tubes, providing for smoother sliding action and better tactile feedback to the practitioner.

BRIEF DESCRIPTION OF THE DRAWINGS

The invention will now be described in greater detail by way of reference to the following drawings, wherein:

FIG. 1 is a perspective view of one embodiment of a regulating device in accordance with the present invention as utilized in conjunction with a CSE set, showing the spinal needle in a retracted state;

FIG. 2 is a perspective view of the regulating device of FIG. 1, showing the spinal needle advanced through the lumen of the epidural needle;

FIG. 3 depicts an exploded assembly view of the regulating device of FIG. 1;

FIG. 4 illustrates a cut-away side view of the regulating device of FIG. 1, as taken along line 4—4 of FIG. 1, showing the gripping of the spinal needle by the spring element;

FIG. 4a is a partial view of the interaction between the spring element and spinal needle illustrated in FIG. 4;

FIG. 5 is a second cut-away side view of the regulating device of FIG. 1, illustrating actuation of the spring element to release it from engagement with the spinal needle;

FIG. 5a is a partial view of the interaction between the spring element and spinal needle illustrated in FIG. 5;

FIG. 5b depicts formation of a non-closed opening in the spring element;

FIG. 7 is an exploded assembly view of the regulating device of FIG. 6;

FIG. 8 is a cutaway side view of the regulating device of FIG. 6, as seen along line 8—8 of FIG. 6, showing the spring element in its released state with respect to the spinal needle;

FIG. 8a depicts the inner tube disposed relative to the outer tube for sliding point contact;

FIG. 8b is a partial view of the interaction between the spring element and the spinal needle, as illustrated in FIG. 8;

FIG. 9 is a second cutaway side view of the regulating device of FIG. 6, showing the spinal needle grippingly engaged by the spring element;

FIG. 9a is a partial view of the interaction between the spring element and the spinal needle illustrated in FIG. 9;

DETAILED DESCRIPTION OF THE INVENTION

Figure 6:
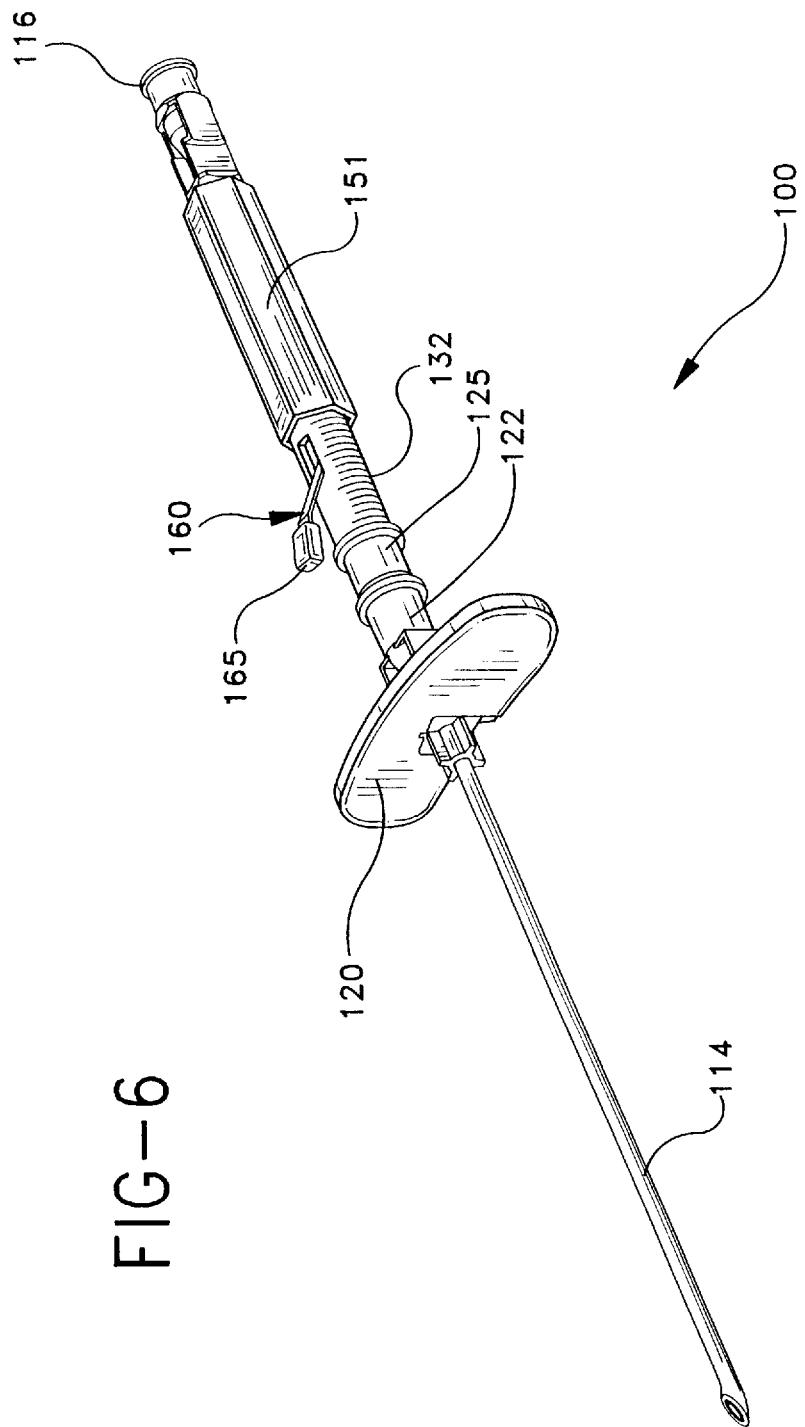
FIG. 6 depicts in perspective view a second embodiment of a regulating device in accordance with the present invention.

Turning now to the drawings, wherein like numerals denote like components, FIGS. 1–5 depict one embodiment of a regulating device 10 for adjusting the extension length of a spinal needle 12 relative to an epidural needle 14 during a CSE procedure. It is understood and intended that while the embodiments discussed herein are described in particular to regulating the extension of a spinal needle relative to an epidural needle during a combined CSE procedure, the device is readily applicable to any device and/or procedure employing a needle through needle technique, particularly where regulation of needle length extensions during that technique are envisioned.

As will be used herein, the term "distal" is meant to convey the direction furthest from the practitioner, while the term "proximal" is intended to convey the direction nearest the practitioner.

Referring to FIGS. 1–5, the overall construction of regulating device 10 in conjunction with an epidural needle 14 and spinal needle 12 is illustrated. Epidural needle 14 will be well known to those skilled in the art and, in general, includes a distal end 14a and a lumen 15 extending through the length of the needle. Distal end 14a of the epidural needle may be curved, for instance, to enhance a practitioner's efforts in directing placement of an epidural catheter (not shown) in the epidural space of a patient. A wing collar 20 may be provided to enable a practitioner to manipulate the epidural needle and/or the overall regulating device 10, during use. Epidural needle 14 further features a female luer connector 22 permitting attachment of epidural needle 14 to an appropriate fitting, a syringe, or the like.

Spinal needle 12, equally well known to the skilled artisan, includes a distal end 12a together with a hub assembly 16. Hub assembly 16 features a fitting element 18 configured to be placed within an appropriate fitting or the like. Spinal needle 12 may also be provided with a stylet (not shown), as is known to those skilled in the art, both for blocking lumen 13 of the spinal needle during insertion and for providing the practitioner with a way to check for CSF during the procedure.

In general, device 10 may be employed with any combination of spinal needle 12 and epidural needle 14. Useful ranges of epidural needle 14 include lengths between 8 centimeters ("cm") (3.1496") to about 8.890 cm (3½"), while spinal needle 12 can range from about 14.645 cm (5 ⁴⁹⁄₆₄") to about 15.558 cm (6 ⅛") in length. Spinal needle 12 can be provided in various standardized diametral sizes ("gauges") depending on the particular anesthetic application desired by the practitioner, but in general it has been found that spinal needles 12 between 22 gauge and 29 gauge will accommodate most applications. The following table provides diametral dimensions across the gauge range:

Table of Hypodermic Tubing Nominal Sizes

| Gauge | Outside Diameter (mm) | Inside Diameter (mm) |
| --- | --- | --- |
| 30 | 0.30 | 0.18 |
| 29 | 0.33 | 0.20 |
| 28 | 0.36 | 0.20 |
| 27 | 0.40 | 0.25 |
| 26 | 0.46 | 0.30 |
| 25 | 0.51 | 0.30 |
| 24 | 0.56 | 0.36 |
| 23 | 0.64 | 0.38 |
| 22 | 0.71 | 0.46 |
| 21 | 0.82 | 0.56 |
| 20 | 0.90 | 0.65 |
| 19 | 1.08 | 0.80 |
| 18 | 1.27 | 0.96 |
| 17 | 1.50 | 1.17 |
| 16 | 1.65 | 1.32 |

A general overall view of regulating device 10 in conjunction with spinal needle 12 and epidural needle 14 is broadly depicted in FIGS. 1–5. In the form depicted, regulating device 10 includes a first sliding member such as an outer cylinder or tube 51 disposed in sliding relation to a second sliding member such as an inner cylinder or tube 32, each of which are respectively fixed to one of spinal needle 12 or epidural needle 14. While other configurations may be envisioned, as here depicted, epidural needle 14 in mounted to inner tube 32 via a hub fitting 25 disposed at the distal end of inner tube 32. Hub fitting 25 includes a proximal end 26 configured to mate with a male luer extension disposed at distal end 28 of inner tube 32, with the hub fitting itself including a male luer fitting 24 at its distal end for snug insertion into hub 22 of the epidural needle. It will be realized by the skilled artisan that hub fitting 25 could be eliminated, with inner tube 32 directly fitted to female hub 22 via male luer extension 30. It will also be realized by those skilled in the art that hub fitting 25 may be provided either as part of the regulating device 10 or as part of the epidural needle 14; likewise, if desired, inner tube 32 could itself be provided as part of epidural needle 14. For instance, inner tube 32 could be formed as an integral part or extension of hub 22.

As herein illustrated, spinal needle 12 may be secured to outer tube 51 via its hub fitting element 18 which may be configured for snug and secure engagement with proximal end 46 of outer tube 51. When assembled, the spinal needle 12 will project through the lumen 15 of epidural needle 14, with distal end 12a of the spinal needle axially extendible relative to distal end 14a of the epidural needle by sliding action between the outer tube 51 and inner tube 32 of the regulating device.

It will be appreciated by the skilled artisan that the device may be configured such that the distal ends 12a, 14a of the spinal and epidural needles, respectively, are first aligned prior to manipulation of the device to regulate the extension of spinal needle 12 relative to epidural needle 14. Alternately, if desired, the device maybe configured such that when assembled, distal end 12a of the spinal needle is pre-extended a user-selectable distance past distal end 14a of the epidural needle, thereafter allowing the practitioner to further extend the spinal needle as desired via actuation of the device. The amount of pre-extension can be selected according to the needs or desires of the practitioner. In either case, while various extension lengths "x" (see FIG. 2) of spinal needle 12 relative to the epidural needle are possible depending on user need or desire, an extension length of approximately 1.501 cm (0.591") (inches) has been found to suffice for applications to most patients. However, one skilled in the art of catheters, needles and hypodermic delivery devices will recognize that for specialty applications such as neonates, pediatric patients, especially thin or obese individuals, and other specialty applications, it may be desirable to reduce or increase the sizes, gauges, component lengths, or extension lengths and/or other dimensions associated with the various components herein described for the specific application.

Inner tube 32 may be formed as a hollow cylindrical tube extending between distal end 28 and a proximal end 29 and defines an outside surface 27. Inner tube 32 can be formed from any appropriate rigid material including a medical grade plastic such as polycarbonate, a metal, or the like, and, if desired, can be formed through an injection molding process. For purposes which will be further elaborated upon herein, inner tube 32 features a slot 36 providing access to interior regions of inner tube 32. While the overall length and diameter of the inner tube 32 may be chosen as need or desire dictate, an outside diameter "a" (FIG. 1) of about 0.620 cm (0.244") and an overall length "c" (FIG. 3) of about 2.009 cm (0.791") measured between distal end 28 and proximal end 29 should suffice for most applications. It will also be appreciated that if distal ends 14a, 12a of the epidural and spinal needles are aligned prior to use, a proximal length "d" (FIG. 3) of inner tube 32 should remain within outside tube 51 to provide stability. Here, a length "d" of about 0.508 cm (0.200") may be provided for stability, with the remaining 1.501 cm (0.591") of inner tube 32 length representing the relative extension of spinal needle 12 relative to epidural needle 14 in use.

A plurality of markings 34 may also be provided on the outside surface of inner tube 32 to help the practitioner gauge the relative extension of outer tube 51 respective of inner tube 32. Markings 34 may be calibrated, as need or desire dictate, to any standard of measurement, such as millimeters, centimeters, inches, or the like. Markings 34 may be calibrated such that indication is given when distal ends 12a, 14a of the spinal and epidural needles, respectively, are fully aligned. Likewise, if spinal needle pre-extension is desired, markings 34 may be calibrated to indicate when the desired length of spinal needle pre-extension has been effected. The markings may also be employed to gauge the overall extension length "x" of spinal needle 12 relative to epidural needle 14.

Outer tube 51 includes a proximal end 46 and a distal end 44 and, as previously described, is disposed in sliding relationship with inner tube 32. Like inner tube 32, outer tube 51 can be formed from a suitable material such as medical grade plastic, metal, or the like, and it can be injection molded. Outer tube 51 includes an inside surface 52 and an outside surface 53. The outside surface 53 of the tube can be shaped in a variety of manners to enable secure gripping by the practitioner. In the embodiment 10 illustrated in FIGS. 1–5, outside surface 51 is round, but as will be discussed for FIGS. 6–9, outside surface 51 can be shaped as a hexagon. Other configurations are equally possible. Moreover, outside surface 53 can be textured or roughened to enhance one's grip on the device. The outer diameter "b" and the length "l" (FIG. 2) of outside tube 51 can be constructed to any appropriate dimension, both to provide easy manipulation by the practitioner and to accommodate the variously sized. epidural needles 14/spinal needles 12 utilized as previously described. In general, an outside diameter "b" of about 0.856 cm (0.3371") and a length "l" of about 2.606 cm (1.026") will suffice for most practitioners. Referring to FIG. 3, if desired a cap 40 may be provided at proximal end 29 of inner tube 32 to be securely mated to the proximal end via an appropriately sized male fitting portion 42. It will be appreciated that cap 40 may be inserted into the distal end 29 of the inner tube 32 during assembly, such that inner tube 32 will be disposed within the interior of the outer tube 51. As the spinal needle 12 is fitted to the proximal end 46 of the outside tube 51, the spinal needle 12 is disposed through the center of cap 40 via an opening 41.

To assist a practitioner in regulating the length of spinal needle 12 relative to epidural needle 14, a spring element 60 is provided in conjunction with inner tube 32. In the configuration shown, spring element 60 may be formed from a flattened piece of spring stock such as spring steel; however, other materials, such as resilient plastics or the like, may be equally contemplated. Likewise, it will be envisioned by the skilled artisan that other configurations, such as pushbutton designs or sliding latch designs, may be incorporated in lieu of the configuration described herein.

Spring element 60 features a fixed end 62 secured in the interior of inner tube 32, for instance, via a screw 66 joining holes 63, 68 formed in the respective spring element and inner tube.. However, it will be apparent to the skilled artisan that other manners of a fixation, such as welding, adhesive techniques, or the like may also be employed. Spring element 60 further includes a free end 64 disposed through slot 36 provided in inner tube 32. A plastic or rubberized tab portion 65 may be affixed to free end 64 to assist the practitioner in manipulating free end 64 when actuation of regulating device 10 is desired. The fixed end 62 of spring element 60 leads into a bend 80 which progresses towards an angle 72 formed in the spring element.

Spring element 60 features one or more passages or openings intermediate the fixed and distal ends 63, 64 respectively, through which spinal needle 12 is threaded, The purpose of the passages or openings is to provide means allowing spring element 60 to securely grip or lock spinal needle 12 relative to epidural needle 14, in a manner that provides a variably continuous locking ability through the range of potential extension lengths "x" of spinal needle 12 relative to epidural needle 14. In the configuration illustrated in FIGS. 4, 4a, 5 and 5a, the one or more openings comprise a distal-most opening 70 and a proximal-most opening 71 disposed on either side of angle 72. Spinal needle 12 is disposed through both the proximal-most and distal-most openings 70, 71, respectively. Angle 72 may be formed to any appropriate orientation, such as an acute angle or an obtuse angle, depending on the dimensions of the various components and their influence on the interaction between spinal needle 12 and the openings of spring element 60. Here, angle 72 is shown as a substantially right angle. It will be appreciated by the skilled artisan that the openings can assume either round or non-round shapes. It will also be realized by the skilled artisan that openings 70, 71 need not be entirely closed, but that they but can be formed to intersect with a side 67 of the spring element. See FIG. 5B.

FIGS. 4 and 4a illustrate spring element 60 in a locked state respective of spinal needle 12. Here, spring element 60 grips spinal needle 12 via interaction of spinal needle 12 with proximal-most opening 71 at an edge 73. It will be appreciated by the skilled artisan that, if desired, distal-most opening 70 could likewise be configured to grip the spinal needle, either in conjunction with the gripping action provided by proximal-most opening 71 or in lieu of it. When it is desired to vary the axial extension of spinal needle 12 relative to epidural needle 14, a practitioner may exert a force "F" upon free end 64 of the spring element. Spring element 60 will flex along bend 80, thrusting proximal-most hole 71 in a downward direction, releasing contact between edge 73 and spinal needle 12 to unlock the spinal needle. See FIGS. 5 and 5a. Hence, spinal needle 12 is free to slide in both of distal-most and proximal-most openings 70, 71, allowing the practitioner to vary the axial position of outer tube 51 respective of inner tube 32 so as to vary the axial extension length "x" of spinal needle 12 relative to epidural needle 14. In the configuration shown, spinal needle 12 is free to pass through distal-most opening 70 in both the locked and unlocked positions.

When the desired axial extension of spinal needle 12 is observed, the practitioner will release force "F" from free end 64, causing spring element 60 to recover its original angular orientation along bend 80, propelling proximal-most hole 71 towards spinal needle 12 such that edge 73 recontacts spinal needle 12, locking the spinal needle in place relative to the epidural needle. By permitting a user-variable extension of outer tube 51 relative to inner tube 32, then, a variably extendible locking arrangement is provided vis-a-vis spinal needle 12 and epidural needle 14.

While it is desirable to maintain a relatively close diametral tolerance between the outside surface 27 of inner tube 32 and the inside surface 52 of outer tube 51 to promote stability and precise sliding action, the inside diameter "F" (FIG. 3) of outer tube 51 should provide a slight clearance to prevent undue friction when sliding relative to the inner tube 32 Here, the diameter "F" may be configured to about 0.627 cm (0.247") to prevent frictional resistance with an inner tube 32 having, for instance, an outside diameter "a" of 0.620 cm (0.244").

FIGS. 6–9 illustrate a second embodiment 100 of the regulating device in accordance with the present invention. For the sake of clarity and to assist the reader, components largely common with embodiment 10 of FIGS. 1–5 have been referred to with the same numeral, save for the addition of a prefix numeral "1." Here, outer tube 151 features an interior surface 152 formed as a plurality of planar surfaces 158, circumferentially disposed around the central axis of the outer tube 151. While here illustrated as formed with a hexagonal configuration having six planar surfaces 158, it will be understood and appreciated by those skilled in the art that the invention is not so limited, and that the interior surface may be configured with any number of planar surfaces such as pentagonal, octagonal, etc. as need or desire dictate. As before, it will be seen that inner tube 132 is disposed within the outer tube 151 such that the outside surface 133 of the inner tube 132 is in substantial sliding contact with planar surfaces 158 of outer tube 151. Unlike the embodiment of FIGS. 1–5, where the outside and inside surfaces, respectively, of inner tube 32 and outer tube 51 are in substantial sliding contact, here, a plurality of contact points 161 are established by the intersection of the relatively rounded outside surface 133 of inner tube 132 and each of planar surfaces 158. See FIG. 8a It will be appreciated that by this arrangement, the contact area between the tubes is reduced. By providing sliding point contact between inner tube 132 and outer tube 151, frictional resistance between the tubes may be substantially reduced, thereby enhancing smooth sliding action between the tubes, and potentially resulting in better tactile feedback to the practitioner.

It will be understood and appreciated that instead of providing the planar surfaces on the interior of the outer tube, with a rounded exterior surface on the inner tube, the plurality of planar surfaces may be structured on the exterior surface of the inner tube, with the interior of the outer tube rounded so as to provide point contact. It will be further understood that the entire length of outer tube 152 need not be structured with planar surfaces 158. Rather, only the axial portion of outer tube 151 which will be subjected to relative sliding motion respective to the inner tube 132 need be structured so as to provide the benefits described above. Thus, for an extension "x" of 1.501 cm (0.591"), only an axial length of 1.501 cm (0.591") measured from the distal end 144 of the outside tube 151 need be provided with the planar surfaces 158.

As seen in FIGS. 6–9, a second version of spring element 160 is disclosed. While here shown associated with the embodiment 100 depicted in FIGS. 6–9, it will be appreciated and understood by the skilled artisan that spring element 160 is equally applicable to embodiment 10 depicted in FIGS. 1–5; likewise, spring element 60 described in FIGS. 1–5 may be employed with embodiment 100. Spring element 160, like spring element 60, may be formed from a flattened piece of spring steel. Like the previous embodiment, spring element 160 includes a fixed end 162 secured to inner tube 132, for instance, by a screw 166, and a free end 164 displaced through a slot 136 formed in inner tube 132. Unlike the previous spring element 60 hereinbefore described, however, spring element 160 is designed such that inner and outer tubes 132, 151 are oriented for free sliding prior to a user's application of force onto free end 164 of the spring element. As illustrated, spring element 160 is bent at an angle 172, forming a base portion 175 affixable to inner tube 132 via screw 166. In lieu of a plurality of openings through which spinal needle 112 is threaded, a single opening 170 is provided intermediate the fixed and free ends 162, 164 of spring element 160. Opening 170 features an engaging edge 173 for locking spinal needle 112 in position relative to epidural needle 114.

In use, as illustrated in FIG. 8, spring element 160 is initially oriented with respect to spinal needle 112 such that spinal needle 112 is free to slide through opening 170. Accordingly, the practitioner may vary the axial position of outer tube 151 relative to inner tube 132 in order to arrive at a desired extension length of spinal needle 112 relative to epidural needle 114. See FIG. 8b. When the desired position is reached, the practitioner may exert a force "F" onto free end 164 of spring element 160, causing the spring element to bend around angle 172, thrusting edge 173 of opening 170 into contact with spinal needle 112 in locking the device. Particularly, slot 136 of inner tube 132 may be provided with a detent or other engaging portion 137, as may be envisioned by the skilled artisan, which securely but releasably retains spring element 160 in its locked position vis-a-vis spinal needle 112. When it is desired to withdraw spinal needle 112 from the patient, the practitioner merely need exert a reverse force onto free end 164, releasing spring element 160 from engagement with detent 137, and allowing the practitioner to retract outer tube 151 relative to inner tube 132.

Operation of the invention will now be explained. For the sake of convenience and to avoid redundancy, reference is made principally to embodiment 10 of FIGS. 1–5. As previously explained, regulating device 10 can be provided either as part of the CSE set including epidural needle 14 and spinal needle 12, or the device may be provided for use with an individual spinal needle or epidural needle separately sourced, or with a prematched CSE set separately sourced. For instance, device 10 can be pre-attached or otherwise form an integral component of either a separately sourced epidural needle 14 or separately sourced spinal needle 12. For instance, device 10 can form the hub portion of a spinal needle 12.

If, for example, the device is provided with a separately sourced CSE set, epidural needle 14 is first affixed to inner tube 32 via hub fitting 25 as previously described, with inner tube 32 thereafter slid through outer tube 51. If provided, cap 40 may thereafter be fitted to distal end 29 of the inner tube to secure the inner tube against inadvertent withdrawal of outer tube 51. The spinal needle 12 may thereafter be fitted to the outer tube 51, and inserted through the hole 41 in the cap 40 (if so provided). The spinal needle will project through the interiors of both outer tube 51 and inner tube 32. In order that the spinal needle pass through both distal-most and proximal-most openings 70,71, the practitioner may depress free end 64 of spring element 60, such that edge 73 of proximal-most opening 71 does not contact spinal needle 12. In this manner, spinal needle 12 will pass through the one or more openings 70, 71 in the spring element and rest disposed through lumen 15 of the epidural needle 14. It will be understood that if provided as part of a CSE set, the regulating device 10 may be pre-assembled together with the spinal needle 12 and epidural needle 14.

Figure 11:
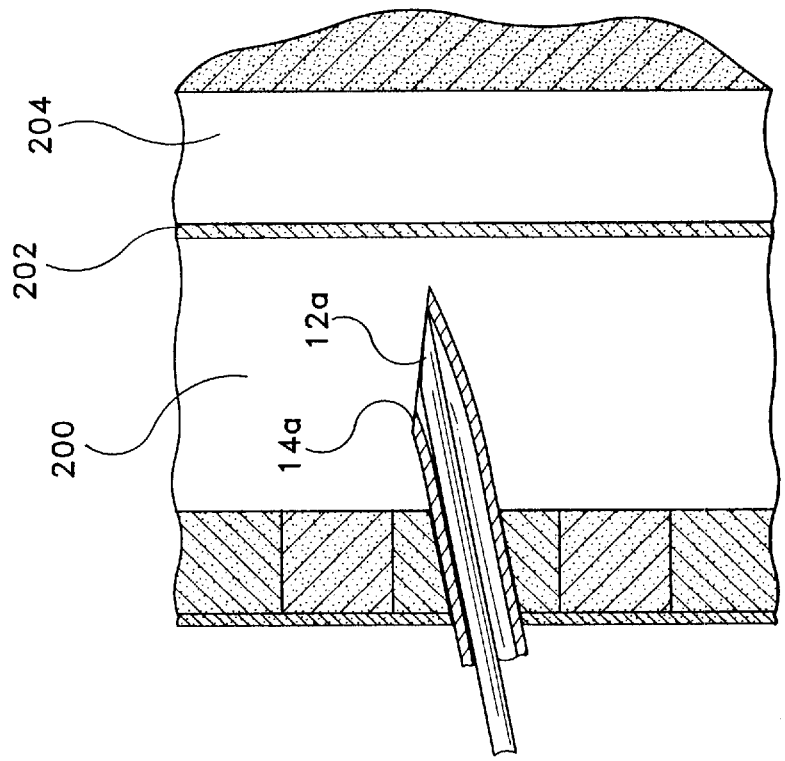
FIG. 11 is a side view illustrating placement of a spinal needle within the lumen of the epidural needle and alignment of the distal tips of both needles prior to extension of the spinal needle.

In order to provide the practitioner with an effective way to gauge the axial extension of the spinal needle 12 relative to the epidural needle 14, the dimensions of the various components such as the inner tube 32 and outer tube 51 may be chosen so that in initial locked position of spring element 60, the distal tip 12a of the spinal needle is aligned with the distal tip 14a of the epidural needle, as illustrated in FIG. 11. As a practical matter, this may be accomplished by designating one of markings 34 on inner tube 32, such that by aligning distal end 44 of the outer tube 51 with that marking, the practitioner may be assured that the distal tips are aligned and from there gauge the relative extension of spinal needle 12 vis-a-vis epidural needle 14.

In use, with the spinal and epidural needles aligned as previously described, the set is inserted into the epidural space 200 of the patient until the distal point 14a of the epidural needle is positioned by the practitioner in an appropriate location in the epidural space. Note that in this position, outer tube 51 is extended relative to the inner tube 32 so that the spinal needle 12 is in a retracted state (FIGS. 1 and 4), with distal tips 12a, 14a of the spinal and epidural needles being aligned.

When the epidural needle has been properly positioned, spring element 60 may be activated (depressed) by the practitioner, releasing proximal-most opening 71 from engagement with spinal needle 12, thereby permitting outer tube 51 to be axially slidable in the distal direction with respect to the inner tube 32. Note that the practitioner will depress spring element 60 with one hand, while manipulating outer tube 51 with the other hand. Inner tube 32, itself fixed to the epidural needle 14, will remain fixed relative to the patient. As earlier described, a practitioner may additionally utilize the hand actuating spring element 60 to manipulate wing collar 20, providing additional support to the epidural needle 14, if need or desire dictate.

Figure 12:
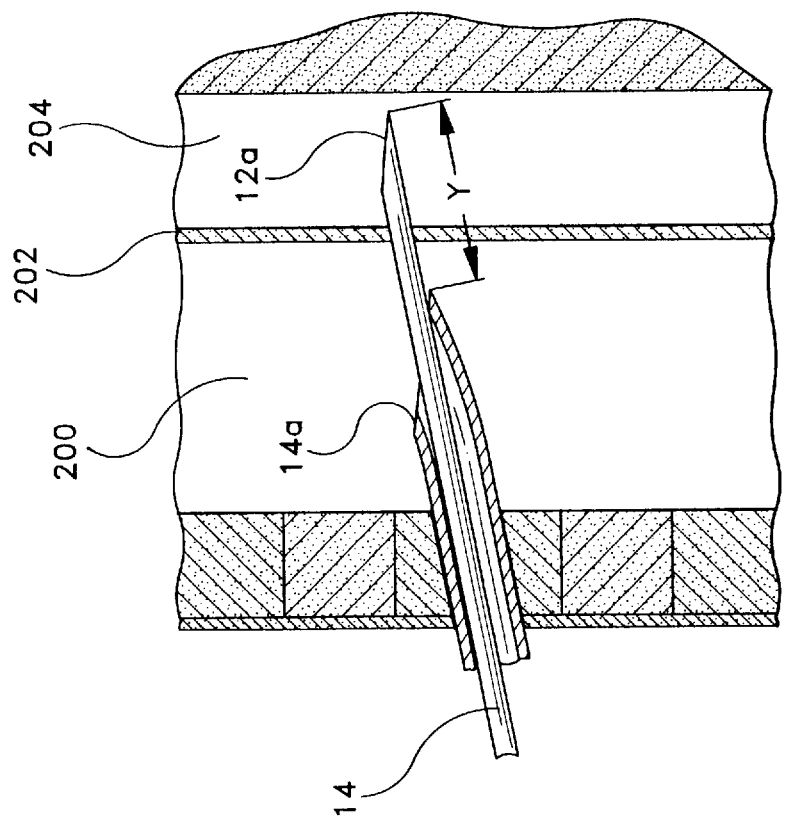
FIG. 12 is a side view illustrating extension of the spinal needle through the dura mater of a patient into the subarachnoid space.

By continuing to slide outer tube 51 distally axially forward, spinal needle 12 will be extended through the epidural needle 14 (FIGS. 2 and 5) so as to puncture the dura mater 202 and come to rest in the subarachnoid space 204 (FIG. 12). Again, the practitioner may monitor the relative position of distal end 44 of the outer tube 51 relative to the markings 34 as a means to assess relative insertion of the spinal needle. As earlier described, the dimensions of the various components may be chosen and selected as need or desire dictate so that the spinal needle 12 will have a relative extension "X" (see FIG. 2) relative to the spinal needle 14 when the outer tube 51 has been slid axially forward to a maximum position. Intermediate extension positions "Y" (see FIG. 12) may be selected by the practitioner based on the relative position of distal end 44 of outer tube 51 to inner tube 32.

Upon selecting the appropriate position, the practitioner will release force "F" against spring element 60, causing spring element 60 to recover around angle 72, forcing opening 70 (and particularly edge 73) to engage spinal needle 12. The position of the outer tube 51 is then locked relative to the inner tube 32. If a stylet has been provided, the same may be removed by the practitioner to detect for CSF. It will also be appreciated that by providing a rotating fit between the male luer fitting 24 and hub 22 of epidural needle 14, and/or a rotating fit between the male luer extension 30 of inner tube 32 and hub fitting 25, the practitioner will be able to rotate the spinal needle in all four quadrants of the subarachnoid space 202 while maintaining the spinal needle in locked position relative to the epidural needle.

Figure 10:
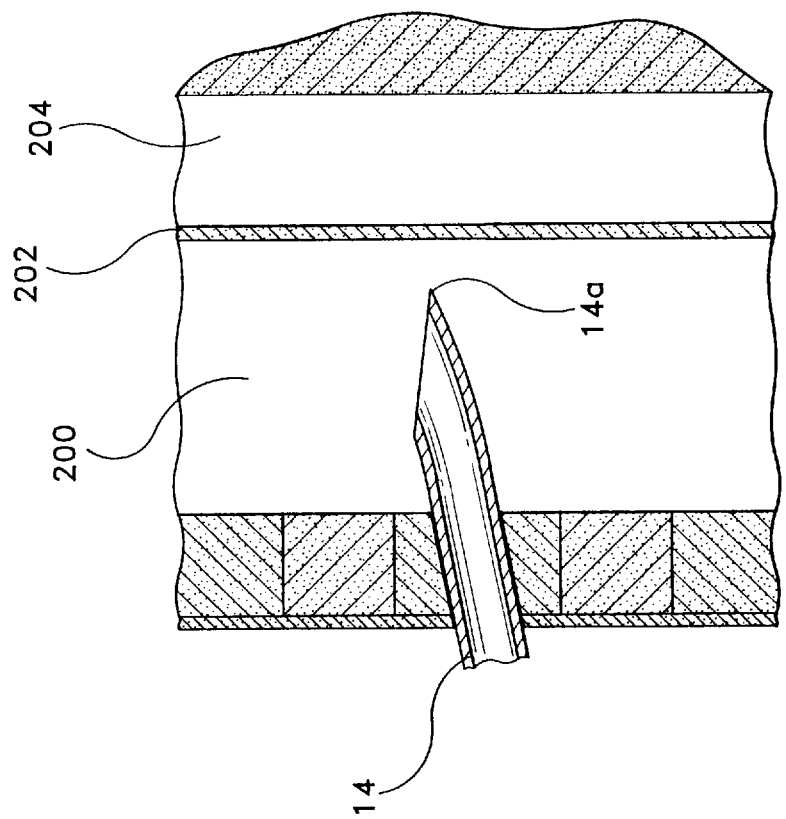
FIG. 10 is a side view illustrating placement of an epidural needle into the epidural space of a patient.

While not illustrated in FIGS. 10–12, an alternate configuration is to select a desired pre-extension length of spinal needle 12 relative to epidural needle 14, in which case one (or more) of markings 34 can be designated to indicate when the desired pre-extension length has been effected. The epidural needle would first be located in the epidural space, with the spinal needle thereafter fitted to the outer tube and through the epidural needle in the manner previously described, with the distal end of the spinal needle extended past the distal end of the epidural needle to the desired pre-extension length. If the desired pre-extension of the spinal needle has not placed distal end 12a in the subarachnoid space 204, then the practitioner may actuate the device to further extend spinal needle 12 relative to epidural needle 14, all in the manner previously described.

Figure 13:
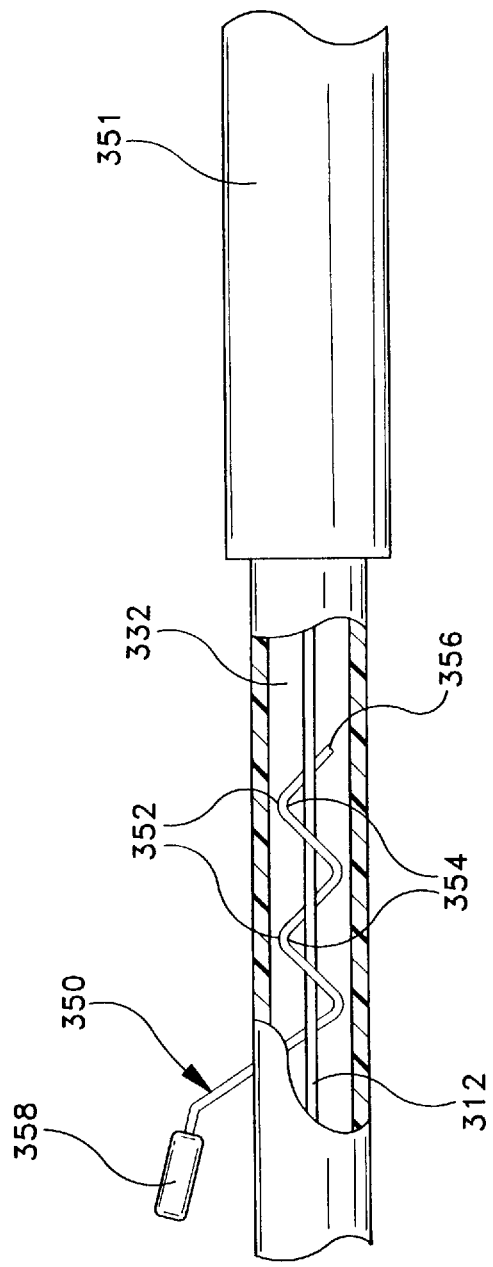
FIG. 13 depicts in partial perspective view a third embodiment of a regulating device in accordance with the present invention.

An alternate configuration of the device is seen in FIG. 13 Here, in lieu of a spring element having one or more passages or holes formed in the body of the spring element, a coil spring 350 is provided to grip spinal needle 312. Coil spring 350 features a free end 358 disposed through a slot (not shown) formed in inner tube 332, and a fixed end 356 attached to an interior location of inner tube 332. Coil spring 350 includes a plurality of turns 352 intermediate the fixed and free ends that are disposed around spinal needle 312. The plurality of turns define a plurality of throughways 354. circumferentially disposed about spinal needle 312. Coil spring 350 can be configured such that in the locked position, one or more of coil turns 352 engages spinal needle 312, thereby locking the position of spinal needle 312 relative to the epidural needle (not shown). When free end 358 of the coil spring is appropriate manipulated, spinal needle 312 will be free to pass within throughways 354, allowing the practitioner to displace outer tube 351 relative to inner tube 332, thereby regulating the extension of the spinal needle relative to the epidural needle, as desired.

Thus, it will be seen that the regulating device as described herein provides the practitioner with a ready and sure way to practice a CSE procedure in a safe and sure manner. The device is easily operable and will guide the practitioner to accurate, continuously variable spinal needle extensions while providing him or her with smooth, steady sliding action and, hence, valuable tactile feedback. The spinal needle may be easily manipulated with one hand while actuating the spring element with the other.

It will be appreciated and understood by those skilled in the art that additional and further forms of the invention may be devised without departing from the spirit and scope of the appended claims, the invention not being limited to the specific embodiments shown.

What is claimed is:

1. A device for regulating the extension of a spinal needle relative to an epidural needle, comprising:

a first member for securing an epidural needle;

a second member defining an internal cavity comprising a plurality of planar surfaces substantially circumferentially disposed about a central axis of said second member, said first member comprising an exterior surface in point contact with said planar surface and slidably disposed relative to said first member for securing said spinal needle; and a spring element for selectably locking said spinal needle relative to said epidural needle, said spring element having one end fixed to said first member, a free end manipulable by a practitioner, and at least one passage defined intermediate the fixed and free ends of the spring element, said spinal needle disposed through said at least one passage, wherein said spring element is deflectable between a locked position, wherein a portion of said spring element adjacent said at least one passage is disposed to engage the spinal needle so that said first member is locked relative to said second member, and an unlocked position, wherein said at least one passage is disposed to permit the spinal needle to freely slide therethrough allowing said second member to slide relative to said first member to regulate the extension of the spinal needle relative to the epidural needle.

2. The device of claim 1, wherein said first member is a tube.

3. The device of claim 1, wherein said second member is a tube.

4. The device of claim 1, wherein said at least one passage comprises two passages.

5. A device for regulating the extension of a spinal needle relative to an epidural needle, comprising:

an inner tube having proximal and distal ends and a sidewall defining an exterior surface, an interior surface, a slot through the sidewall, and a cavity therein, said distal end being disposed to be securable to a hub of an epidural needle;

an outer tube having proximal and distal ends and defining a second cavity, the exterior surface of said inner tube substantially slidably disposed within the second cavity of said outer tube, a hub of a spinal needle being securable to the proximal end of said outer tube so that when the spinal needle is mounted within the epidural needle having said inner tube distal end secured to the hub of the epidural needle said spinal needle passes through the cavity of the inner tube; and a spring element for selectably locking said spinal needle relative to said epidural needle, said spring element having one end fixed to said inner tube, a free end disposed through the slot for manipulation by a practitioner, and at least one opening intermediate the fixed and free ends of the spring element through which the spinal needle passes, said spring element deflectable between a locked position, wherein a portion of said spring element adjacent said at least one opening engages the spinal needle to lock the position of the spinal needle relative to the epidural needle, and an unlocked position, wherein said at least one opening is oriented to permit free sliding of the spinal needle through the opening, such that said outer tube is axially slidable relative to said inner tube to vary the axial extension of said spinal needle relative to said epidural needle.

6. The device of claim 5, wherein said spring element is formed with a non-straight length defining an angle intermediate the fixed and free ends.

7. The device of claim 5, wherein said at least one opening is substantially non-round in shape.

8. The device of claim 6, wherein said slot comprises a detent for retaining said spring element in said locked position.

9. The device of claim 5, wherein said spring element is formed with a non-straight length having an angle intermediate the fixed and free ends, said at least one opening comprising two openings located on either side of the angle.

10. The device of claim 9, wherein said two openings comprises a distal-most opening and a proximal-most opening, wherein said distal-most opening is configured to permit the spinal needle to slide in both the locked and unlocked positions of the spring element, and wherein the proximal-most opening grips the spinal needle when the spring element is in its locked position.

11. The device of claim 5, wherein said inner tube includes a plurality of markings formed along the axis of the inner tube for gauging the axial position of said outer tube relative to said inner tube.

12. The device of claim 5, wherein said epidural needle is secured to said inner tube by a fitting located at the distal end of the inner tube.

13. The device of claim 5, wherein the second cavity of said outer tube comprises a plurality of planar surfaces substantially circumferentially disposed around the central axis of the outer tube, wherein the exterior surface of said inner tube is configured for point contact with said planar surfaces.

14. The device of claim 1, wherein said first member is an integral component of said epidural needle.

15. The device of claim 5, wherein said inner tube is an integral component of said epidural needle.

16. A method for regulating the extension of a spinal needle relative to an epidural needle, comprising the steps of:

forming a user-regulatable combined spinal epidural needle set by separately affixing said spinal needle to an outermost sliding member and affixing said epidural needle to an innermost sliding member, said members being substantially concentrically disposed about each other and wherein said spinal needle is slidingly disposed in the lumen of said epidural needle;

providing a spring element having an opening selectably engageable with said spinal needle to selectably lock said spinal needle relative to said epidural needle, said spring element having one end affixed to the sliding member that is affixed to the epidural needle and a free end manipulable by a practitioner; and moving the sliding members relative to one another to regulate the extension of said spinal needle relative to said epidural needle.

17. The method of claim 16, wherein said step of regulating the extension of said spinal needle relative to said epidural needle further comprises the step of moving said outermost sliding member relative to a set of markings formed on said innermost sliding member, said markings calibrated to the degree of extension of said spinal needle relative to said epidural needle.

18. The method of claim 16, wherein said step of separately affixing comprises the steps of affixing said innermost sliding member to said epidural needle, locating said epidural needle in the epidural space of a patient, and subsequently sliding said outermost sliding member over said innermost sliding member such that said spinal needle passes through the lumen of said epidural needle.

19. The method of claim 16, further including the step of forming sliding surfaces on each of said sliding members, the sliding surfaces disposed in point contact with one another.

20. The method of claim 16, wherein said step of moving the sliding members comprises actuating the spring element with the hand supporting the innermost sliding member and sliding the outermost sliding member relative to the innermost sliding member with the other hand.

21. The method of claim 16, further comprising the step of aligning the distal tips of said spinal needle and said epidural needle prior to said step of regulating the extension of the spinal needle relative to the epidural needle.

22. The method of claim 16, further comprising the step of providing a pre-extension of said spinal needle relative to said epidural needle prior to said step of regulating the extension of the spinal needle relative to the epidural needle.

* * * * *